(12) United States Patent
Kimura et al.

(10) Patent No.: US 10,909,671 B2
(45) Date of Patent: Feb. 2, 2021

(54) REGION OF INTEREST WEIGHTED ANOMALY DETECTION

(71) Applicant: INTERNATIONAL BUSINESS MACHINES CORPORATION, Armonk, NY (US)

(72) Inventors: Daiki Kimura, Tokyo (JP); Ryuki Tachibana, Yokohama (JP)

(73) Assignee: International Business Machines Corporation, Armonk, NY (US)

( * ) Notice: Subject to any disclaimer, the term of this patent is extended or adjusted under 35 U.S.C. 154(b) by 6 days.

(21) Appl. No.: 16/149,722

(22) Filed: Oct. 2, 2018

(65) Prior Publication Data

US 2020/0104990 A1 Apr. 2, 2020

(51) Int. Cl.
*G06T 7/00* (2017.01)
*G16H 30/20* (2018.01)
(Continued)

(52) U.S. Cl.
CPC .......... *G06T 7/0002* (2013.01); *G06F 16/285* (2019.01); *G06F 16/51* (2019.01);
(Continued)

(58) Field of Classification Search
CPC ......... G06T 7/0002; G06T 2207/20084; G06T 1/00; G06T 2207/10072; G06T 3/4046; G06T 7/35; G06T 2210/41; G06T 7/0012; G06T 7/11; G06T 2200/04; G06T 2207/20081; G06T 2207/10076; G06T 17/00; G06T 19/20; G06T 2207/20101; G06T 19/003; G06T 2200/24; G06T 15/205; G06T 7/12; G06T 7/174; G06F 16/51; G06F 16/285; G06F 17/10; G06F 40/289; G06F 16/2455; G06F 17/18; G06F 30/20; G06F 3/011; G06F 40/205; G06F 19/321; G06F 19/3456; G06F 19/00; G06F 19/324; G06F 11/1448; G06F 16/22; G06F 21/316; G06F 21/32; G06F 17/11; G06F 17/15; G06F 17/16; G06F 2111/10;
(Continued)

(56) References Cited

U.S. PATENT DOCUMENTS 9,495,594 B2 11/2016 Rosario et al.
10,387,445 B2 8/2019 Limonad et al.
(Continued)

OTHER PUBLICATIONS

Grace Period Disclosure—Narita, Minori, et al. "Spacially-weighted anomaly detection," Yokohama, Jun. 2018, 4 Pages.
(Continued)

*Primary Examiner* — Nimesh Patel
(74) *Attorney, Agent, or Firm* — Tutunjian & Bitetto, P.C.; Randall Bluestone

(57) ABSTRACT

Anomalies are detected by generating a reconstructed dataset from an original dataset by using a generative model, calculating a differential dataset between the original dataset and the reconstructed dataset as a differential dataset, determining at least one of a region of interest of the original dataset and a region of interest of the reconstructed dataset, weighting the differential dataset by using the determined region of interest, and detecting an anomaly by using the weighted differential dataset.

20 Claims, 11 Drawing Sheets

(51) Int. Cl.
*G06K 9/62* (2006.01)
*G06K 9/48* (2006.01)
*G06N 3/08* (2006.01)
*G06F 16/51* (2019.01)
*G06F 16/28* (2019.01)

(52) U.S. Cl.
CPC ......... *G06K 9/481* (2013.01); *G06K 9/6215* (2013.01); *G06K 9/6232* (2013.01); *G06K 9/6284* (2013.01); *G06N 3/08* (2013.01); *G16H 30/20* (2018.01); *G06T 2207/20084* (2013.01)

(58) Field of Classification Search
CPC ............. G06F 3/04815; G06F 3/04842; G06F 3/04847; G06F 16/50; G06F 40/279; G06K 9/6232; G06K 9/6215; G06K 9/481; G06K 9/6284; G06K 9/6256; G06K 9/00228; G06K 9/00335; G06K 9/621; G06K 9/6218; G06K 9/6262; G06K 9/6255; G06K 2209/05; G06K 9/00147; G06K 9/4671; G06K 9/6267; G06K 9/6292; G06K 9/66; G06K 9/52; G06K 9/6201; G06K 9/627; G06K 2209/40; G06K 9/00369; G06K 9/00288; G06K 9/00577; G06K 9/00201; G06K 9/00342; G06K 9/00664; G06N 3/08; G06N 3/0454; G06N 3/0472; G06N 3/0445; G06N 3/084; G06N 7/005; G06N 20/00; G06N 20/10; G06N 3/0481; G06N 3/088; G06N 5/02; G06N 20/20; G06N 3/04; G06N 5/022; G06N 7/00; G06N 3/063; G06N 3/10; A61B 2562/0219; A61B 5/112; A61B 5/1114; A61B 5/6813; A61B 5/6824; A61B 5/7264; A61B 5/7275; A61B 5/744; A61B 6/032; A61B 6/5205; A61B 6/03; A61B 8/4416; A61B 8/5261; A61B 6/027; A61B 6/52; A61B 5/00; A61B 5/7267; A61B 2576/00; A61B 5/743; A61B 6/469; A61B 34/10; A61B 34/20; A61B 6/502; A61B 8/08; A61B 8/0808; A61B 8/0825; A61B 5/7282; G16B 5/00; G16B 15/00; G16B 25/00; G16B 35/00; G16H 10/60; G16H 30/20; G16H 50/70; G16H 40/00; G16H 70/00; G16H 50/20; G16H 50/30; G16H 30/40; G16H 50/00; G16H 50/50; G16H 20/00; G16H 10/40; G01N 30/02; G01N 2030/008; G01N 2030/885; G01N 30/88; G01N 33/5044; G01N 33/86; H04L 67/42; H04L 41/16; H04L 43/026; H04L 43/04; H04L 47/2441; H04L 63/0861; H04L 63/1408; C12Q 2537/165; C12Q 1/6869; C12Q 2535/122; C12Q 2545/114
See application file for complete search history.

(56) References Cited

U.S. PATENT DOCUMENTS

| | | | |
|---|---|---|---|
| 10,672,115 | B2 | 6/2020 | Panda et al. |
| 2012/0188342 | A1* | 7/2012 | Gervautz ............... G06T 7/246 348/46 |
| 2014/0101611 | A1* | 4/2014 | Lang ...................... G06F 21/32 715/813 |
| 2014/0232862 | A1 | 8/2014 | Bala et al. |
| 2016/0239972 | A1* | 8/2016 | Zhu ....................... G06T 7/0014 |
| 2017/0316285 | A1 | 11/2017 | Ahmed et al. |
| 2018/0018553 | A1* | 1/2018 | Bach ..................... G06K 9/6247 |
| 2018/0020978 | A1* | 1/2018 | Kaifosh ............... G06K 9/6287 702/150 |
| 2018/0101784 | A1* | 4/2018 | Rolfe ..................... G06N 3/084 |
| 2018/0165554 | A1* | 6/2018 | Zhang .................. G06K 9/6269 |
| 2018/0247201 | A1* | 8/2018 | Liu ........................... G06T 1/00 |
| 2019/0087728 | A1* | 3/2019 | Agarwal ............. G06F 16/2455 |
| 2019/0219994 | A1* | 7/2019 | Yan ..................... G05B 23/0254 |
| 2020/0034654 | A1* | 1/2020 | Mansi .................... G06K 9/621 |

OTHER PUBLICATIONS

Grace Period Disclosure—Kimura, Daiki, et al. "Spatially-weighted anomaly detection with regression model," Meeting on Image Recognition and Understanding, Sapporo, Aug. 2018, 4 pages.
Chattopadhyay, Aditya, et al. "Grad-cam++: Generalized gradient-based visual explanations for deep convolutional networks," arXiv preprint arXiv, Oct. 2017, 14 pages, 1710.11063.
An, Jinwon, et al. "Variational autoencoder based anomaly detection using reconstruction probability," Special Lecture on IE 2, Dec. 2017, pp. 1-18.
He, Kaiming, et al. "Deep residual learning for image recognition," Proceedings of the IEEE conference on computer vision and pattern recognition, 2016, pp. 770-778.
Marin, Giulio, et al. "Hand gesture recognition with leap motion and kinect devices," Image Processing (ICIP), 2014 IEEE International Conference on. IEEE, Oct. 2017, pp. 1565-1569.
Hou, Xianxu, et al. "Deep feature consistent variational autoencoder," Applications of Computer Vision (WACV), 2017 IEEE Winter Conference on. IEEE, Mar. 2017, pp. 1133-1141.
Selvaraju, Ramprasaath R., et al. "Grad-CAM: Visual Explanations from Deep Networks via Gradient-Based Localization," ICCV, Oct. 2017, pp. 618-626, 24 pages.
Chandola, Varun, et al. "Anomaly detection: A survey," ACM computing surveys (CSUR), Jul. 2009, 58 pages, 41,3.
Yamaguchi, Haruyasu, et al. "Yamaguchi fox-pigeon imitation test: a rapid test for dementia," Dementia and geriatric cognitive disorders, 2010, pp. 254-258, 29, 3.

* cited by examiner

Original Dataset

Reconstructed Dataset

Differential Dataset

Weighted Dataset

Normalized Dataset

1st ROI

Integrated ROI

2nd ROI

Known Positive

Known Negative

Unknown Negative

REGION OF INTEREST WEIGHTED ANOMALY DETECTION

STATEMENT REGARDING PRIOR DISCLOSURES BY THE INVENTOR OR A JOINT INVENTOR

The following disclosure(s) are submitted under 35 U.S.C. 102(b)(1)(A):

DISCLOSURE(S): "Spacially-weighted anomaly detection", Minori Narita, Daiki Kimura, Ryuki Tachibana, Symposium on Sensing via Image Information, Yokohama, Jun. 13, 2018; and "Spatially-weighted anomaly detection with regression model", Daiki Kimura, Minori Narita, Asim Munawar, Ryuki Tachibana, Meeting on Image Recognition and Understanding, Sapporo, Aug. 5, 2018.

BACKGROUND

Technical Field

The present invention relates to region of interest weighted anomaly detection.

Description of the Related Art

Visual anomaly detection is common in several applications such as medical screening and production quality check. For example, reconstruction-based detection methods and classification-based detection methods are known. However, the reconstruction-based detection methods are prone to be affected by noise while the classification-based detection methods sometimes fail to detect anomalies in unknown classes. In order to improve accuracy of anomaly detection, a large amount of computational resources and/or time may be required.

SUMMARY

According to an aspect of the present invention, a computer-implemented method is provided that includes: generating a reconstructed dataset from an original dataset by using a generative model; calculating a differential dataset between the original dataset and the reconstructed dataset as a differential dataset; determining at least one of a region of interest of the original dataset and a region of interest of the reconstructed dataset; weighting a differential dataset by using the determined region of interest; and detecting an anomaly by using the weighted differential dataset.

The foregoing aspect may also include an apparatus configured to perform the computer-implemented method, and a computer program product storing instructions embodied on a computer-readable medium or programmable circuitry, that, when executed by a processor or the programmable circuitry, cause the processor or the programmable circuitry to perform the method.

The summary clause does not necessarily describe all features of the embodiments of the present invention. Embodiments of the present invention may also include sub-combinations of the features described above. These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein.

DETAILED DESCRIPTION

Hereinafter, example embodiments of the present invention will be described. The example embodiments shall not limit the invention according to the claims, and the combinations of the features described in the embodiments are not necessarily essential to the invention.

Figure 1:
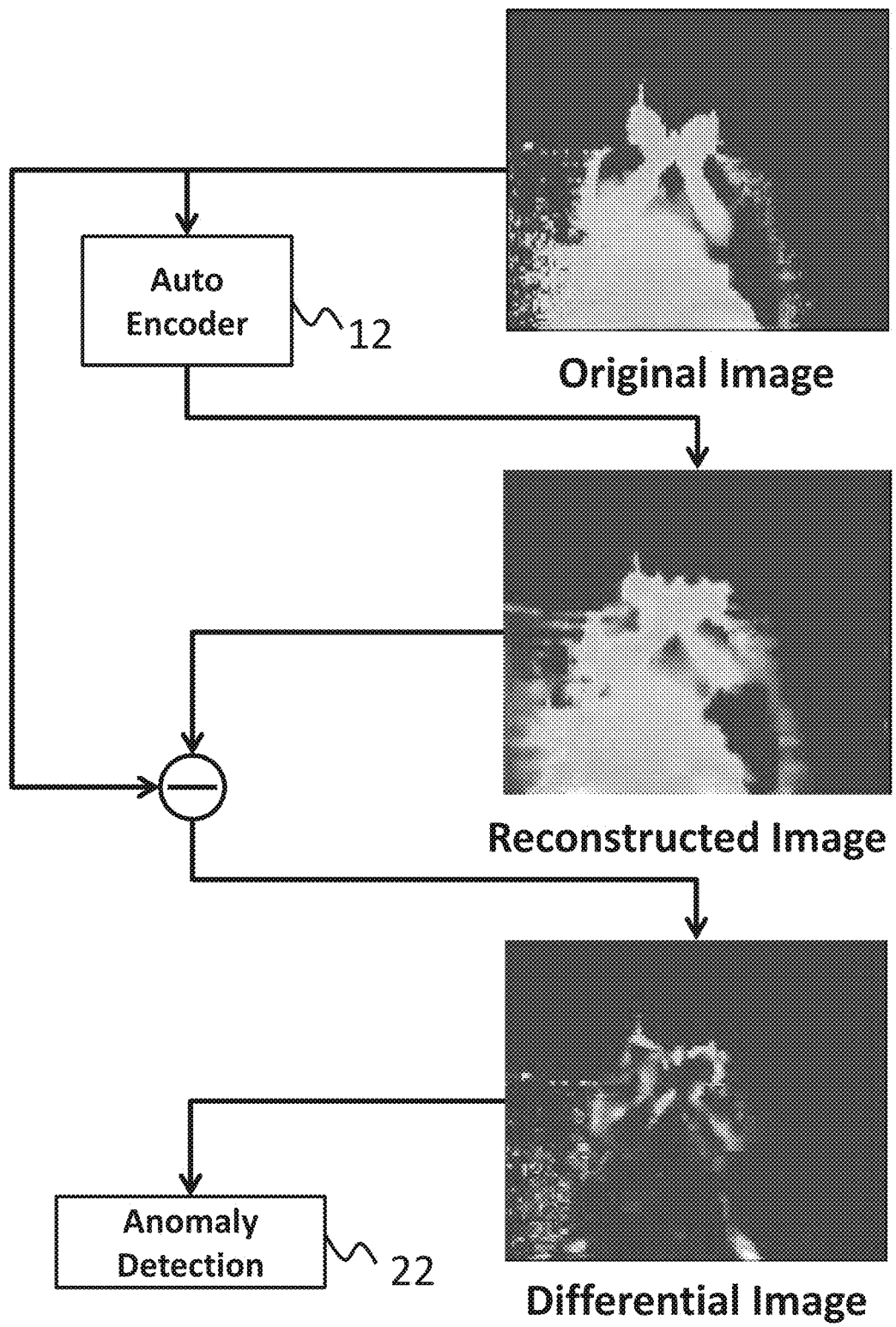
FIG. 1 shows an exemplary framework of an embodiment related to the present invention.

FIG. 1 shows an exemplary framework of an embodiment related to the present invention. In the framework, anomaly is detected by a reconstruction-based method.

In the framework, an autoencoder 12 may first encode an original image (shown as "Original Image") into a latent vector and then decode the latent vector into a reconstructed image (shown as "Reconstructed Image"). Then a differential image between the original image and the reconstructed image (shown as "Differential Image") is calculated. An anomaly detection 22 detects an anomaly if a summation of the differential image is large enough (e.g., exceeds a threshold value).

Figure 2:
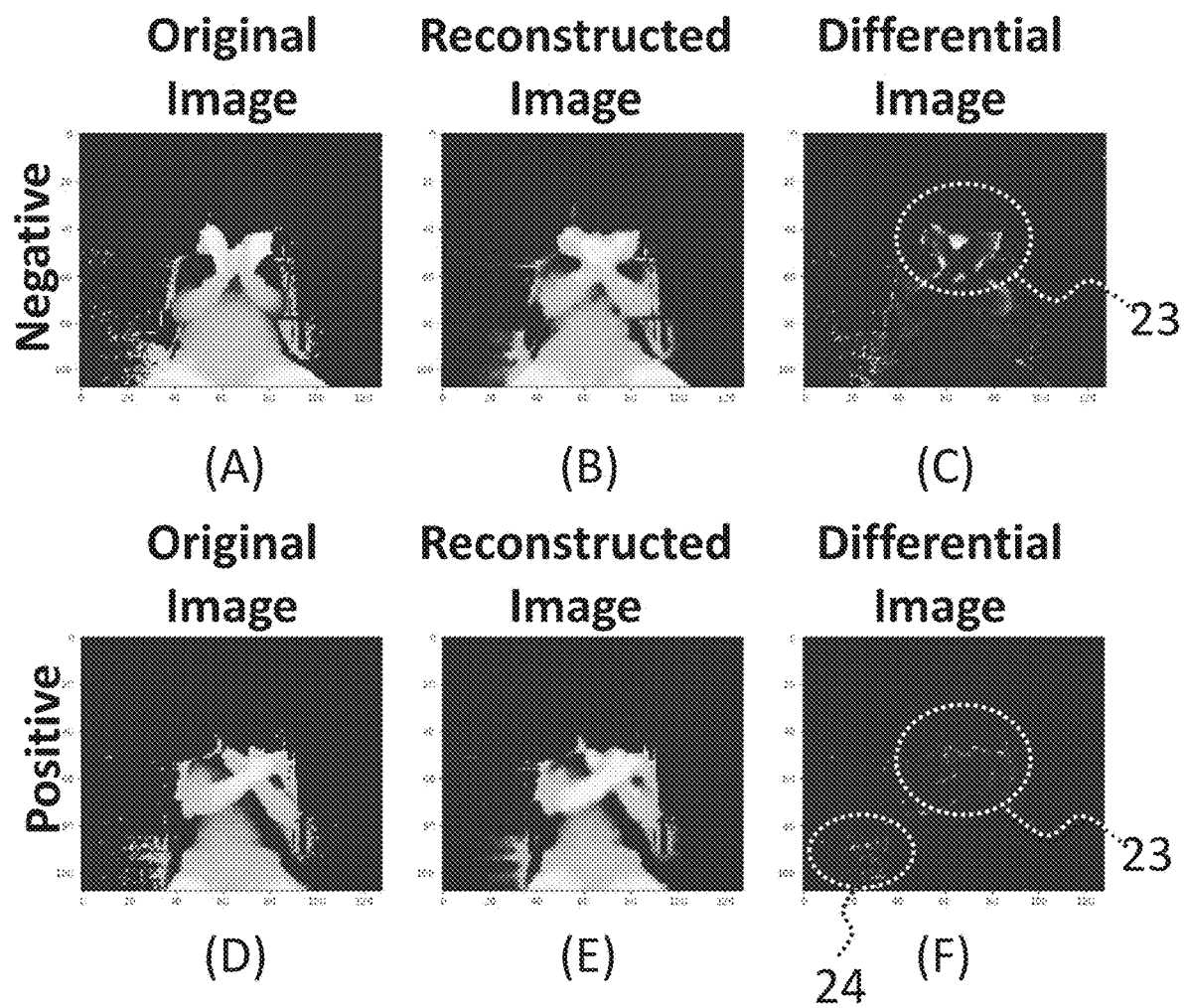
FIG. 2 shows images in the embodiment related to the present invention.

FIG. 2 shows images in the embodiment related to the present invention. Original Image (A) is anomalous (or Negative). For example, Reconstructed Image (B) is reconstructed from Original Image (A). Differential Image (C) represents a difference between Original Image (A) and Reconstructed Image (B). In the embodiment of FIG. 2, Differential Image (C) has a region 23 that shows a large amount of difference. Therefore, Original Image (A) may be identified as anomalous.

In FIG. 2, Reconstructed Image (E) is reconstructed from Original Image (D). Original Image (D) is normal (or Positive). Differential Image (F) represents a difference between Original Image (D) and Reconstructed Image (E). Since a generative model such as the autoencoder 12 averages the original image, noise included in the original image tends to disappear. Therefore, Differential Image (F) includes a noise 24 due to Original Image (D).

A region 23 in Differential Image (F) includes a small amount of difference. Therefore, Original Image (F) could be identified as normal. However, since Differential Image (F) has the noise 24, Differential Image (F) may be identified as anomalous.

Figure 3A:
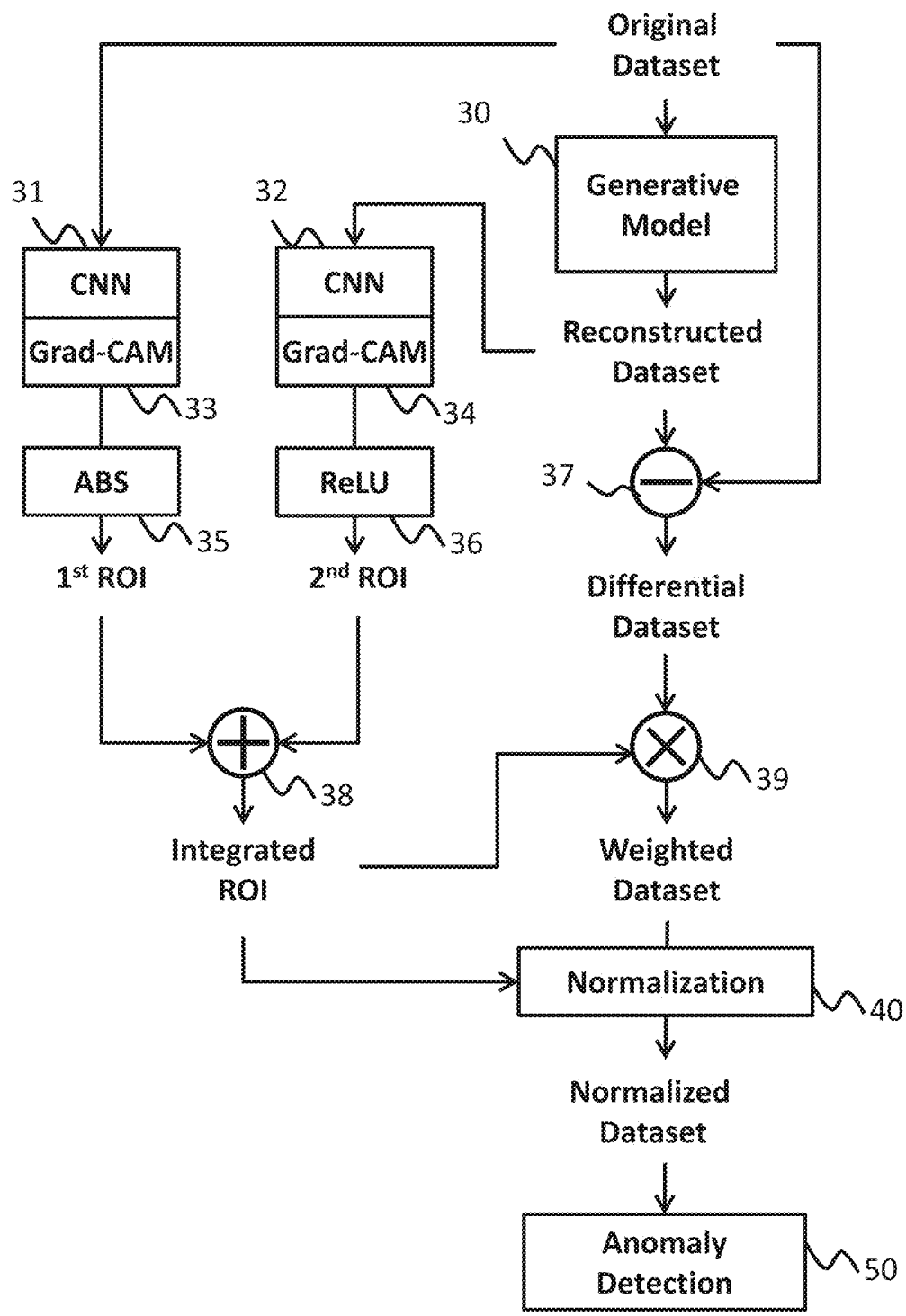
FIG. 3A shows an exemplary framework, according to an embodiment of the present invention.

FIG. 3A shows an exemplary framework, according to an embodiment of the present invention. In the framework, anomalies may be detected by a reconstruction-based method with an incorporation of region of interest (or ROI) perspectives.

In the framework, generative model 30, such as an autoencoder, may first encode an original dataset (shown as "Original Dataset") into a latent vector and then decode the latent vector into a reconstructed dataset (shown as "Reconstructed Dataset"). A differential dataset between the original dataset and the reconstructed dataset (shown as "Differential dataset") is calculated at differential operator 37.

Meanwhile, ROI of the original dataset may be determined by Convolutional Neural Network (CNN 31) and Gradient-weighted Class Activation Mapping (Grad-CAM 33). CNN 31 may be a Convolutional Neural Network that classifies an input dataset as anomalous (or negative) or normal (or positive). Grad-CAM 33 may identify ROI of the input dataset when CNN 31 classifies the input dataset.

Similarly ROI of the reconstructed dataset may be determined by CNN 32 and Grad-CAM 34. In an embodiment, CNN 32 may be the same as the CNN 31. In an embodiment, Grad-CAM 34 may be the same as Grad-CAM 33.

Absolute value (ABS) function 35 is applied to an output of Grad-CAM 33, and then an activated ROI of the original dataset (shown as "$1^{st}$ ROI") is given. Rectified Linear Unit (ReLU) function 36 is applied to an output of Grad-CAM 34, and then an activated ROI of the reconstructed dataset (shown as "$2^{nd}$ ROI") is given. The $1^{st}$ ROI and $2^{nd}$ ROI are integrated by operator 38 to an integrated ROI (shown as "Integrated ROI").

The differential dataset is weighted with the integrated ROI by operator 39 to generate a weighted dataset (shown as "Weighted Dataset"). The weighted dataset is normalized to generate a normalized dataset (shown as "Normalized Dataset") by a normalization 40. Anomaly detection 50 may detect an anomaly by using the normalized dataset. For example, the anomaly detection 50 may detect an anomaly if a summation of the normalized dataset exceeds a threshold.

Figure 3B:
FIG. 3B shows images of the embodiment of the present invention.
Figure 3B:
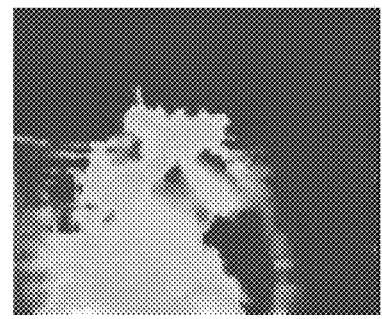
Figure 3B:
Figure 3B:
Figure 3B:
Figure 3B:
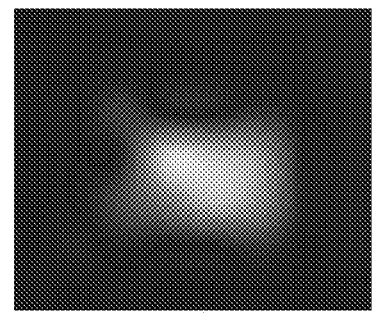
Figure 3B:
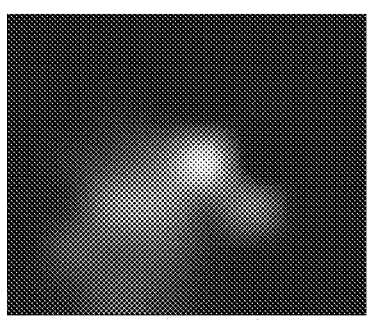
Figure 3B:
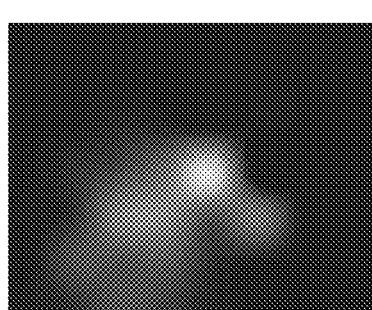

FIG. 3B shows images representing Original Dataset, Reconstructed Dataset, Differential Dataset, $1^{st}$ ROI, $2^{nd}$ ROI, Integrated ROI, Weighted Dataset, and Normalized Dataset. As shown in FIG. 3B, Differential Dataset includes noise in a lower-left region, which may cause a false anomaly detection. However, after the weighting and normalization, the Normalized Dataset includes very little noise in the lower-left region.

According to the framework of FIGS. 3A-3B, an anomaly is detected by using a differential dataset after weighting this with ROIs. As such, the framework may enable accurate detection of the anomaly by removing the noise from ROIs with less computational resources compared with a framework that uses only a massive generative model. In other words, in order to achieve the accuracy of the framework of FIGS. 3A-3B, conventional methods (e.g., generative model based method) need much more computational costs and training data than the framework of FIGS. 3A-3B.

Figure 4:
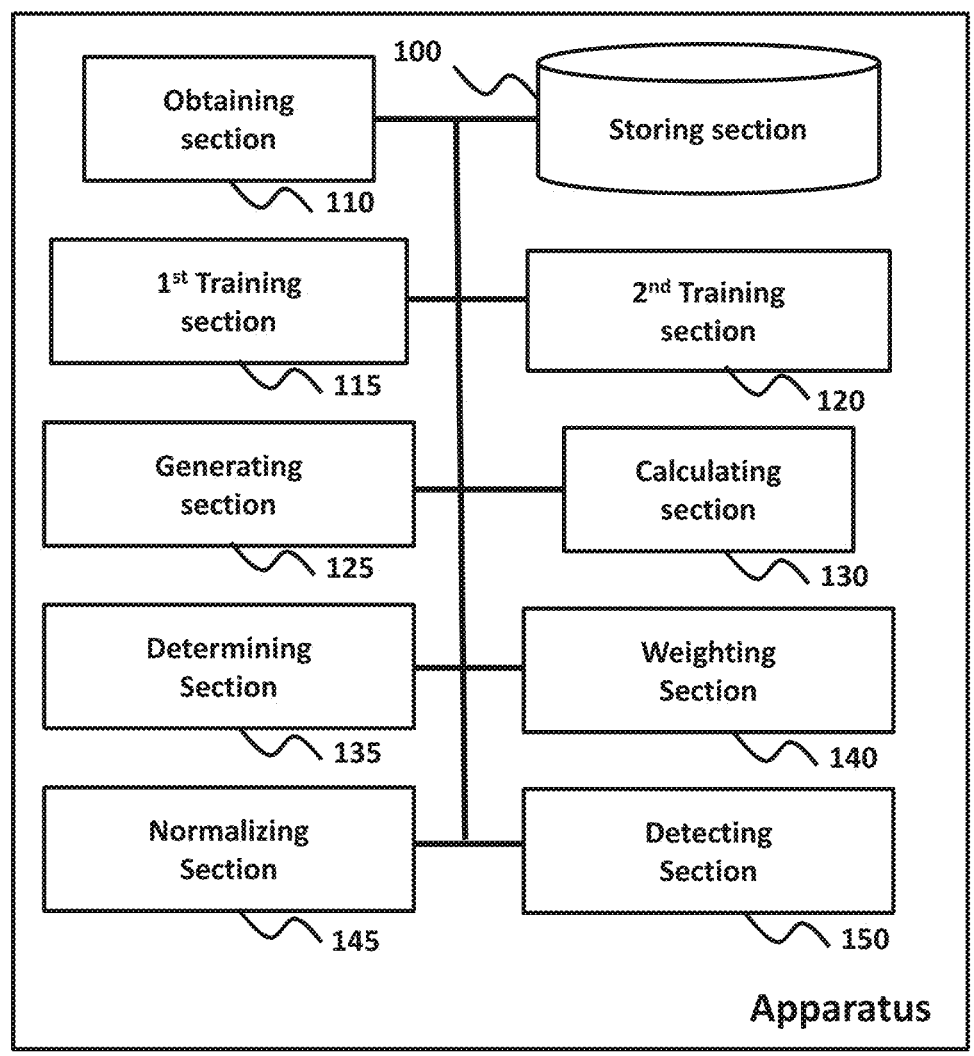
FIG. 4 shows an exemplary configuration of an apparatus 10, according to an embodiment of the present invention.

FIG. 4 shows an exemplary configuration of an apparatus 10, according to an embodiment of the present invention. The apparatus 10 at least partially implements the framework described in FIGS. 3A-3B. Thereby, the apparatus 10 detects an anomaly among a plurality of datasets.

The apparatus 10 may include a processor and/or programmable circuitry. The apparatus 10 may further include one or more computer readable mediums collectively including instructions.

The instructions may be embodied on the computer readable medium and/or the programmable circuitry. The instructions, when executed by the processor or the programmable circuitry, may cause the processor or the programmable circuitry to operate as a plurality of operating sections.

Thereby, the apparatus 10 may be regarded as including a storing section 100, an obtaining section 110, a $1^{st}$ training section 115, a $2^{nd}$ training section 120, a generating section 125, a calculating section 130, a determining section 135, a weighting section 140, a normalizing section 145, and a detecting section 150. In some embodiments, the apparatus 10 may be implemented by two or more computers.

The storing section 100 stores information used for the processing that the apparatus 10 performs. The storing section 100 may also store a variety of data/instructions used for operations of the apparatus 10. One or more other elements in the apparatus 10 (e.g., the obtaining section 110, the $1^{st}$ training section 115, the $2^{nd}$ training section 120, the generating section 125, the calculating section 130, the determining section 135, the weighting section 140, the normalizing section 145, and the detecting section 150) may communicate data directly or via the storing section 100, as necessary.

The storing section 100 may be implemented by a volatile or non-volatile memory of the apparatus 10. In some embodiments, the storing section 100 may store a generative model, a classification model, an original dataset, a reconstructed dataset, a differential dataset, a region of interest, a weighted dataset, a normalized dataset, parameters and other data related thereto.

The obtaining section 110 obtains data used for operations of the apparatus 10. For example, the obtaining section 110 may obtain an original dataset, a training data for a generative model and/or a classification model.

The $1^{st}$ training section 115 trains a generative model (e.g., Variational AutoEncoder) with training data. The generative model may encode an original dataset (e.g., a depth image) into a latent vector and decode the latent vector into a reconstructed dataset (e.g., a reconstructed depth image).

The $2^{nd}$ training section 120 trains a classification model (e.g., Convolutional Neural Network) with training data. The classification model may classify the original dataset as anomalous or normal.

The generating section 125 generates a reconstructed dataset from an original dataset by using the generative model trained by the $1^{st}$ training section 115. In the embodiment, the generating section 125 may encode the original dataset with an encoder of the Variational AutoEncoder to generate a latent vector, and decode the latent vector with a decoder of the Variational AutoEncoder to generate the reconstructed dataset. The generating section 125 may correspond to the generative model 30 in FIG. 3A.

The calculating section 130 calculates a differential dataset between the original dataset and the reconstructed dataset. The calculating section 130 may correspond to the operator 37 in FIG. 3A.

The determining section 135 determines at least one of an ROI of the original dataset and an ROI of the reconstructed dataset. The determining section 135 may correspond to CNN 31, CNN 32, Grad-CAM 33, Grad-CAM 34, ABS 35, ReLU 36, and the operator 38 in FIG. 3A.

The weighting section 140 weights the differential dataset by using the ROI determined by the determining section 135. In an embodiment, the weighting section 140 may emphasize a difference in the differential dataset especially in the ROI of the original dataset and/or reconstructed dataset by the weighting. The weighting section 140 may correspond to the operator 39 in FIG. 3A.

The normalizing section 145 normalizes the weighted differential dataset before detecting the anomaly by using the determined ROI. The normalizing section 145 may correspond to the normalization 40 in FIG. 3A.

The detecting section 150 detects an anomaly by using the weighted differential dataset. The detecting section 150 may detect the anomaly by using the weighted differential dataset normalized by the normalizing section 145.

In an embodiment, the detecting section 150 detects the anomaly if a summation of the weighted differential dataset exceeds a threshold. The detecting section 150 may correspond to the anomaly detection 50.

Figure 5:
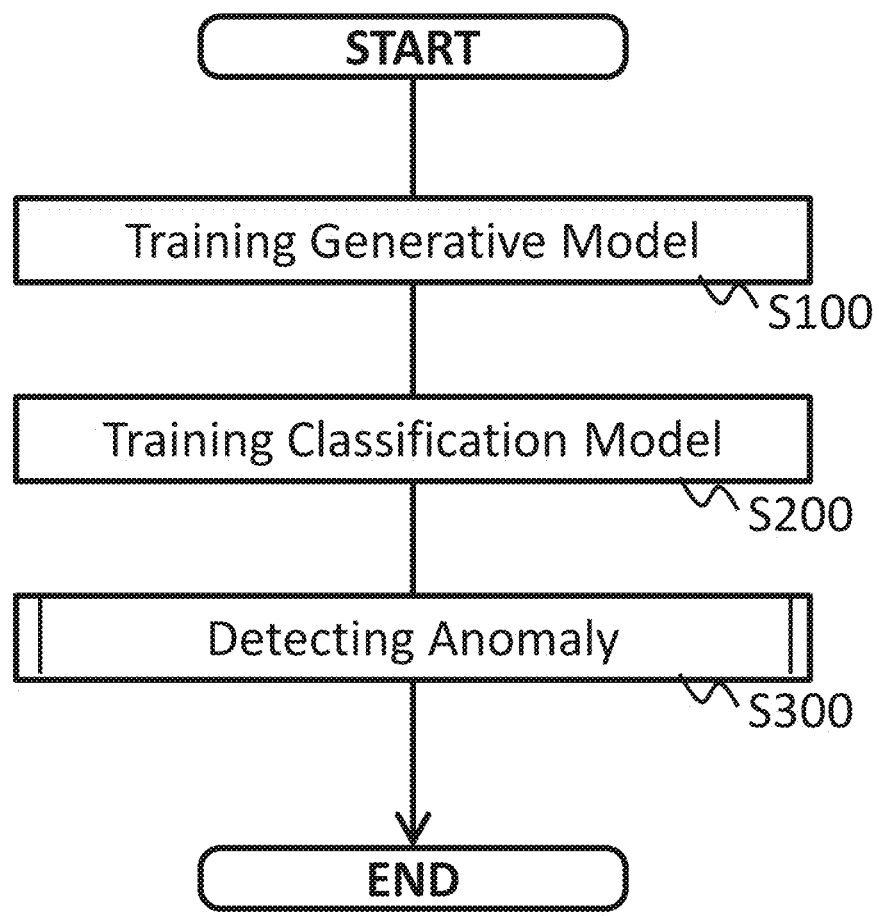
FIG. 5 shows an operational flow according to an embodiment of the present invention.

FIG. 5 shows an operational flow according to an embodiment of the present invention. The present embodiment describes an example in which an apparatus, such as the apparatus 10, performs operations from S100 to S300, as shown in FIG. 5.

At block S100, a $1^{st}$ training section, such as the $1^{st}$ training section 115, trains a generative model for an original dataset. The generative model may compress dimensions of an original dataset and then reconstruct a dataset so as to maintain information of the original dataset as much as possible. In an embodiment, the $1^{st}$ training section may train a conventional Autoencoder or Variational AutoEncoder as the generative model.

The dataset is a sequence of data. In an embodiment, the dataset may be image data such as 2D image data or 3D image data. The 2D image data may be grayscale image data, color (e.g., RBG) image data, or depth data. In an embodiment, the dataset may be audio data or text data of a certain language (e.g., natural language, machine language, etc.).

In an embodiment, the dataset representing the audio data may be a spectrum of sound. In the embodiment, the dataset may be a power spectrum, cepstrum, or, Mel-Frequency Cepstrum Coefficients (MFCC) of the sound. In an embodiment, the dataset representing the text data may be a bag of words generated from the text data. In the embodiment, the apparatus may treat the bag of words as an image data.

At block S200, a $2^{nd}$ training section, such as the $2^{nd}$ training section 120, trains a classification model for an original dataset. The classification model may classify an input dataset as anomalous or normal. The classification model may be a neural network, such as Convolutional Neural Network (or CNN).

Figure 6:
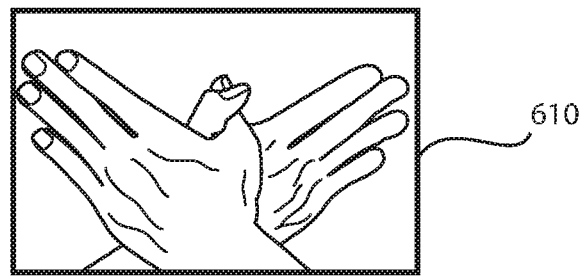
FIG. 6 shows images used for training according to an embodiment of the present invention.
Figure 6:
Figure 6:
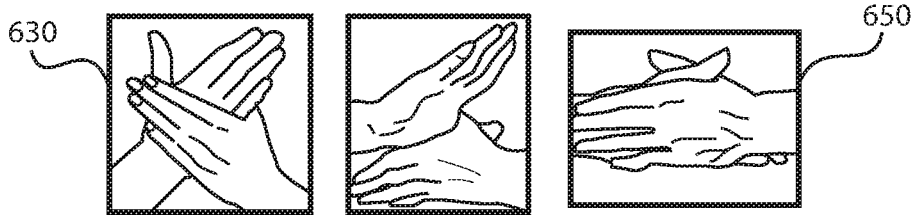

FIG. 6 shows images used for training according to an embodiment of the present invention. FIG. 6 shows 7 images, one of which is known positive 610 and 6 of which are known and unknown negatives 620, 630, 640, 650, 660, and 670. The known positive 610 is normal. The known negative 620 and the unknown negatives 630-670 are anomalous. For example, only the known positive 610 is a correct hand sign, and other negatives 620-670 are incorrect hand signs.

At block S100, the $1^{st}$ training section may train the generative model by using only the known positive 610 such that the generative model reconstructs the known positive 610. In embodiments where the generative model is trained without the negatives, the generative model may be able to handle any unknown negatives without prejudice.

At block S200, the $2^{nd}$ training section may train the classification model by using the known positive 610 and the known negative 620. Since it may not be possible to prepare all varieties of negatives at the training, such embodiments of the $2^{nd}$ training section may use only known negatives.

At block S300, an apparatus, such as the apparatus 10, detects anomalies by using the generative model trained at block S100 and the classification model trained at block S200. Details of block S300 are explained in relation to FIG. 7.

Figure 7:
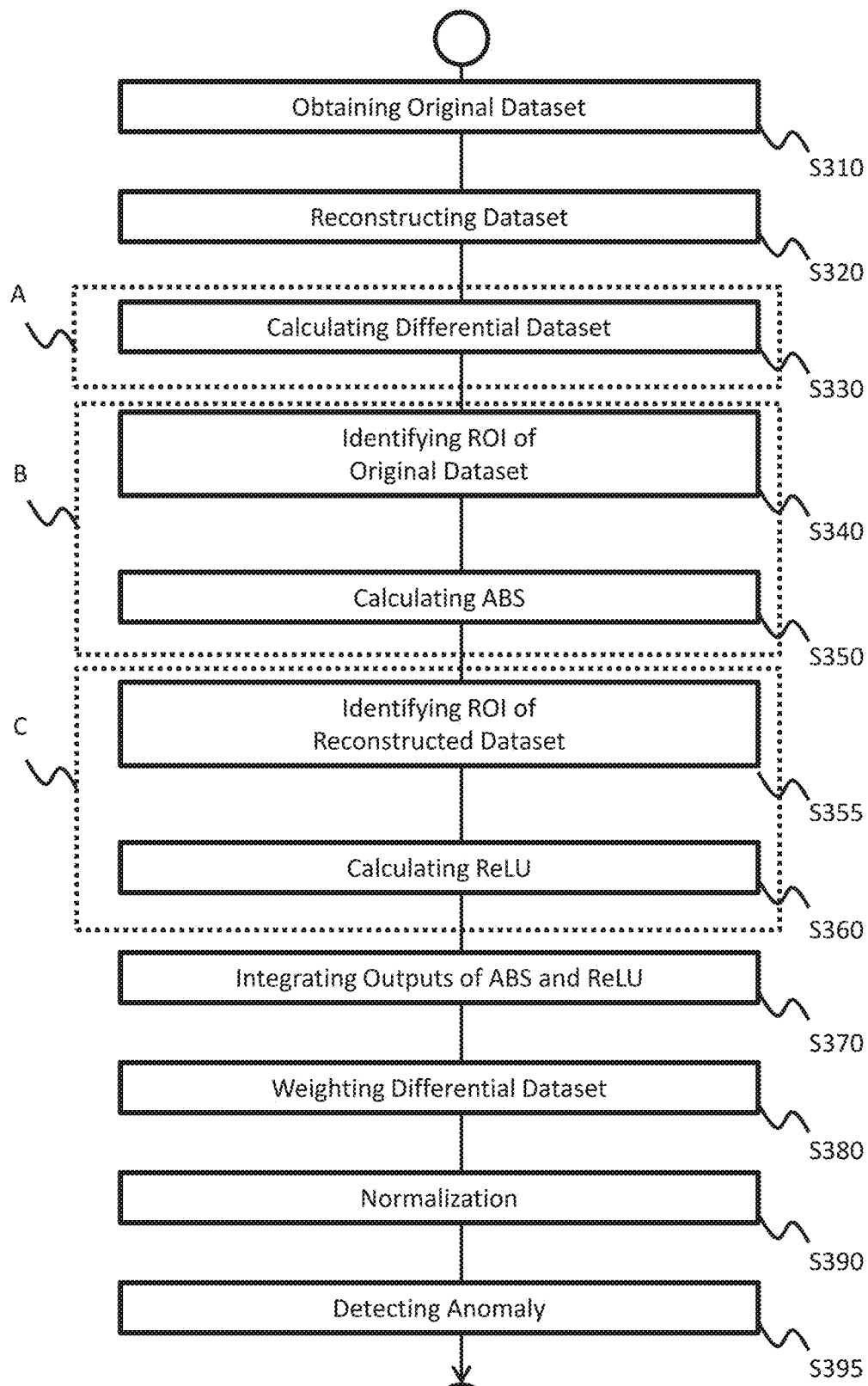
FIG. 7 shows a sub-flow of S300 in the flow of FIG. 5 according to an embodiment of the present invention.

FIG. 7 shows a sub-flow of block S300 in the flow of FIG. 5 according to an embodiment of the present invention. The apparatus performs operations of blocks S310-S395 of FIG. 7 at the operation block S300 of FIG. 5.

At block S310, an obtaining section, such as the obtaining section 110, obtains the original dataset. In an embodiment, the original dataset may be image data, such as 2D image data or 3D image data. In an embodiment, the original dataset may be audio data or text data of a certain language (e.g., natural language, machine language, etc.).

At block S320, a generating section, such as the generating section 125, generates a reconstructed dataset from the original dataset by using the generative model trained at block S100. In an embodiment, the generating section may encode the original dataset with an encoder of a Variational AutoEncoder trained at block S100 to generate a latent vector, and decode the latent vector with a decoder of the Variational AutoEncoder to generate the reconstructed dataset.

At block S330, a calculating section, such as the calculating section 130, calculates a differential dataset between the original dataset obtained at block S310 and the reconstructed image generated at block S320. The calculating section may subtract the reconstructed dataset from the original dataset to generate a differential dataset as the difference between the original and reconstructed datasets. In an embodiment, the calculating section may calculate a difference between a pixel value in a pixel of the original image and the pixel value in a corresponding pixel of the reconstructed image for each pixel.

At block S340, a determining section, such as the determining section 135, determines ROIs of the original dataset. The determining section may generate a saliency map of the original dataset by using the classification model. In an embodiment, the determining section may first classify the original dataset as anomalous or normal by using the classification model trained at block S200. In an embodiment, the determining section may classify the original dataset as one of normal and anomalous by using the CNN.

The determining section may further determine ROIs of the original dataset when the original dataset is classified. In an embodiment, the determining section may apply Grad-CAM to the CNN to obtain a Grad-CAM output as the ROI of the original dataset. In the embodiment, the determining section may apply Grad-CAM to the operation of classification of the original dataset by the CNN to identify ROIs.

At block S350, the determining section applies a first activating function to the ROI of the original dataset to obtain a first output. The first activating function may return a positive value in response to receiving both a positive value and a negative value.

In an embodiment, the first activating function may be an ABS function. In an embodiment, the first activating function may be a squaring function. The first output from the first activating function may be regarded as a heat map as shown as "$1^{st}$ ROI" in FIG. 3B.

The ROI of the original dataset may include some anomalous information and some normal information. By using the first activating function, the first output may include both "anomalous" information of the original dataset and "normal" information of the original dataset.

At block S355, the determining section, determines the ROI of the reconstructed dataset. The determining section may generate a saliency map of the reconstructed dataset by using the classification model. In an embodiment, the determining section may first classify the reconstructed dataset as anomalous or normal by using the classification model trained at block S200. In an embodiment, the determining section may classify the reconstructed dataset as one of normal and anomalous by using the CNN. The CNN used for block S355 may be the same as the CNN used for block S340.

The determining section may further determine ROI of the reconstructed dataset when the reconstructed dataset is classified. In an embodiment, the determining section may apply Grad-CAM to the Convolutional Neural Network to obtain a Grad-CAM output as the ROI of the reconstructed dataset. In the embodiment, the determining section may apply Grad-CAM to the operation of classification of the reconstructed dataset by the CNN to identify ROIs.

At block S360, the determining section applies a second activating function to the ROI of the reconstructed dataset to obtain a second output. The second activating function may return a positive value in response to receiving a positive value while not returning a positive value in response to receiving a negative value. The second activating function may return 0 or substantially 0 in response to receiving a negative value.

In an embodiment, the second activating function may be ReLU function. In an embodiment, the second activating function may be a squaring function that returns 0 to a negative input. The second output from the second activating function may be regarded as a heat map as shown as "$2^{nd}$ ROI" in FIG. 3B.

The ROI of the reconstructed dataset may include information consistent with a "normal" dataset. By using the second activating function, the second output may include only "normal" information from the original dataset. Thereby, the second output may not be affected by useless information of the reconstructed dataset.

At block S370, the determining section calculates an integration of the ROI of the original dataset and the ROI of the reconstructed dataset. The integration of the ROI may be referred to as the "integrated ROI." In an embodiment, the determining section may calculate a summation of the first output obtained at block S350 and the second output obtained at block S360 as the integrated ROI. In a specific embodiment, the determining section may calculate a summation of a pixel value in the first output and the pixel value in a corresponding pixel of the second output for each pixel.

At block S380, a weighting section, such as the weighting section 140, weights the differential dataset calculated at block S330 with the integrated ROI calculated at S370. In an embodiment, the determining section may multiply a pixel value in the differential dataset by the pixel value in a corresponding pixel of the integrated ROI, for each pixel. A resultant dataset of block S380 may be referred to as the "weighted differential dataset."

At block S390, a normalizing section, such as the normalizing section 145, normalizes the weighted differential dataset. In an embodiment, the normalizing section may perform the normalization such that an absolute scale of the integrated ROI does not affect the anomaly detection. A resultant dataset of block S390 may be referred to as the "normalized weighted differential dataset."

At block S395, a detecting section, such as the detecting section 150, detects the anomaly by using the normalized weighted differential dataset. In an embodiment, the detecting section may calculate a summation of the normalized weighted differential dataset. Then, the detecting section may determine that the original dataset is anomalous in response to the summation exceeding a threshold.

In another embodiment, the detecting section may classify the weighted differential dataset using a neural network. Then, the detecting section may determine that the original dataset is anomalous on condition that the neural network classifies the weighted differential dataset as anomalous. In the embodiment, the apparatus may preliminarily train the neural network that receives the weighted differential dataset and output the classification.

An exemplary algorithm for the embodiment of FIG. 5 will now be described. The following exemplary algorithm at least partially corresponds to the operational flow of FIG. 5. The apparatus may perform the following exemplary algorithm to detect anomalies.

At first, an image x, trained $\theta_r$ and trained $\theta_v$ are given. The image x may correspond to an original dataset. The trained $\theta_v$ may correspond to parameters (e.g., weights) of a generative model (such as Generative Model 30). In an embodiment, at block S100, the $1^{st}$ training section may train the VAE with the following equations:

$$\{x_i\} \in N \qquad \text{Eq. (1)}$$

$$\theta_v^* = \underset{\theta_v}{\arg\min}\left[-\sum_i \log p\theta_v(x_i)\right] \qquad \text{Eq. (2)}$$

During this minimization, the $1^{st}$ training section may optimize:

$$L(\theta,\phi;x_i) = D_{KL}(q_\Phi(z|x_i)\|p_\theta(z)) + E_{q\Phi(z|x_i)}[\log p_\theta(x_i|z)] \qquad \text{Eq. (3)}$$

where $\theta$ is generative parameters, $\Phi$ is variational parameters, z is a random latent variable. The $1^{st}$ training section may use a normal distribution for the variable space, and thus the generative loss may be a mean-squared error. $\theta_v$ may include both of $\theta$ and $\Phi$.

The trained $\theta_r$ may correspond to parameters (e.g., weights) of a classification model (such as CNN 31 and CNN 32) used for identifying ROI. In an embodiment, at block S200, the $2^{nd}$ training section may train the CNN with the following equations:

$$\{x_i, y_i\} \in N \cup A \qquad \text{Eq. (4)}$$

$$\theta_r^* = \underset{\theta_r}{\arg\min}\sum_i \|y_i - f(x_i;\theta_r)\| \qquad \text{Eq. (5)}$$

where $y_i$ is the label value of $x_i$. When $x_i$ is normal, $y_i$ is 1; when $x_i$ is anomaly, $y_i$ is 0.

Next, a reconstructed image $\hat{x}$ is generated from a generative model $g(x; \theta_r)$. The loss is calculated from $|\hat{x}-x|$. The loss corresponds to a differential dataset.

Next, $\alpha_x$ is calculated from:

$$\alpha_x = \frac{1}{Z}\sum_i \sum_j \frac{\partial y_x^1}{A_x^{ij}}. \qquad \text{Eq. (6)}$$

$\alpha_x$ corresponds the ROI of the original dataset (such as the output of Grad-CAM 33 in FIG. 3A).

Next, $cam_x$ is calculated from:

$$cam_x = \text{Abs}(\Sigma_k \alpha_x^k A^k). \quad \text{Eq. (7)}$$

$cam_x$ corresponds to the first output (such as 1$^{st}$ ROI in FIG. 3A).

Next, $\alpha_{\tilde{x}}$ is calculated from:

$$\alpha_{\tilde{x}} = \frac{1}{Z} \sum_i \sum_j \frac{\partial y_{\tilde{x}}^l}{A_{\tilde{x}}^{ij}}. \quad \text{Eq. (8)}$$

$\alpha_{\tilde{x}}$ corresponds the ROI of the reconstructed dataset (such as output of Grad-CAM 34 in FIG. 3A).

Next, $cam_{\tilde{x}}$ is calculated from:

$$cam_{\tilde{x}} = \text{ReLU}(\Sigma_k \alpha_{\tilde{x}}^k A^k). \quad \text{Eq. (9)}$$

$cam_{\tilde{x}}$ corresponds to the second output (such as 2$^{nd}$ ROI in FIG. 3A).

Next, cam is calculated from:

$$cam = cam_x + cam_{\tilde{x}}. \quad \text{Eq. (10)}$$

cam corresponds to the integrated ROI (such as Integrated ROI in FIG. 3A).

Next, loss$^{sp}$ is calculated from:

$$loss^{sp} = \frac{loss * cam}{\|cam\|}. \quad \text{Eq. (11)}$$

loss*cam corresponds to the weighted differential dataset (such as Weighted Dataset in FIG. 3A), and loss$^{sp}$ corresponds to the normalized weighted differential dataset (such as Normalized Dataset in FIG. 3A).

Next, score is calculated from:

$$score = -\Sigma_i \Sigma_j loss_{(i,j)}^{sp}. \quad \text{Eq. (12)}$$

Finally, the anomaly is detected by score. For example, the detecting section may detect the anomaly when a value of score exceeds a threshold.

Figure 8:
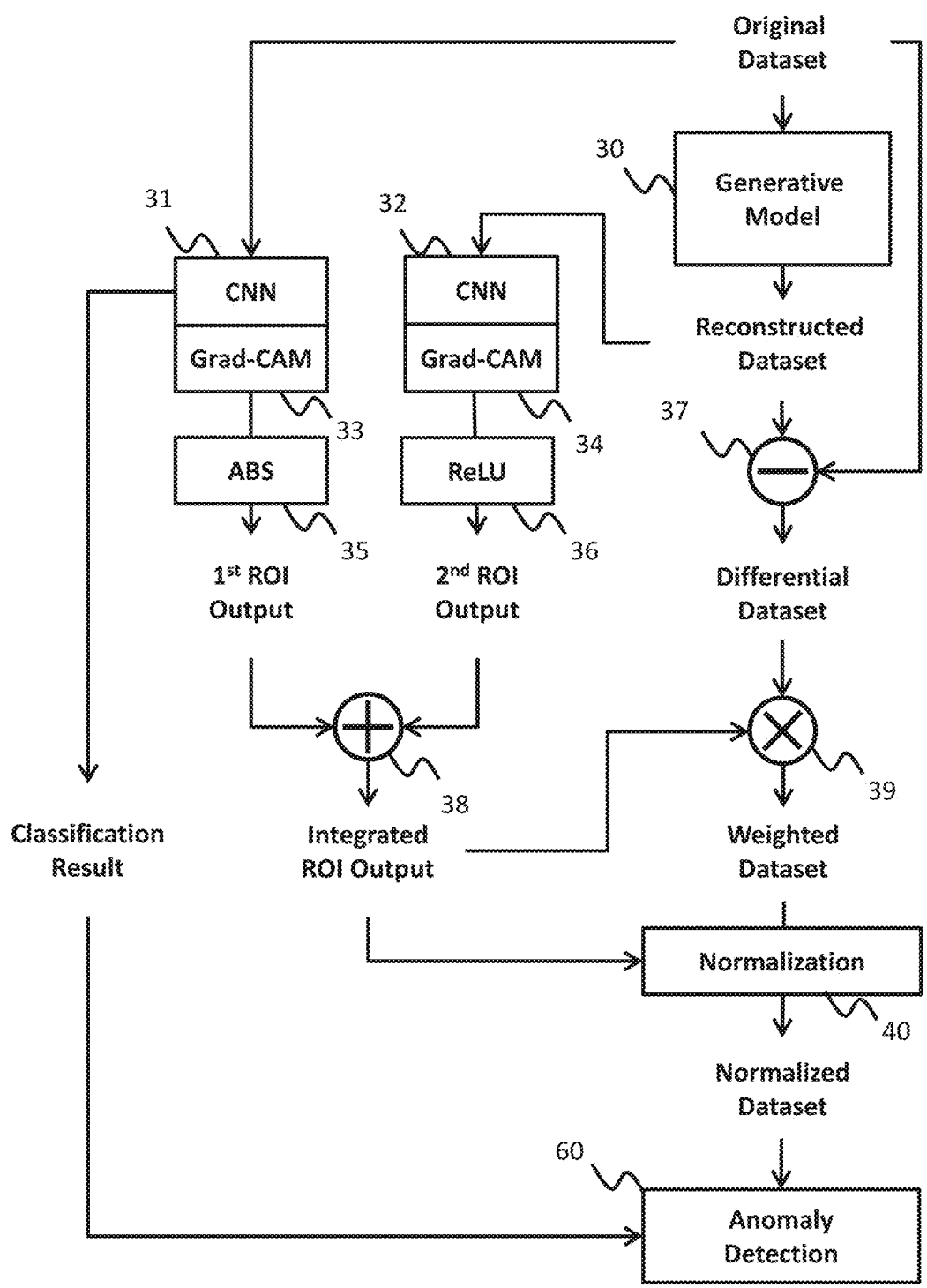
FIG. 8 shows an exemplary framework, according to another embodiment of the present invention.

FIG. 8 shows an exemplary framework, according to another embodiment of the present invention. In this embodiment, an anomaly detection 60, which may correspond to the anomaly detection 50 in FIG. 3A, detects the anomaly by using not only Normalized Dataset but also Classification Result from CNN 31. The other elements and processes in FIG. 8 are substantially similar to the corresponding elements and processes in FIG. 3A, and the image data referenced in FIG. 8 refers to the image data shown in FIG. 3B.

Figure 9:
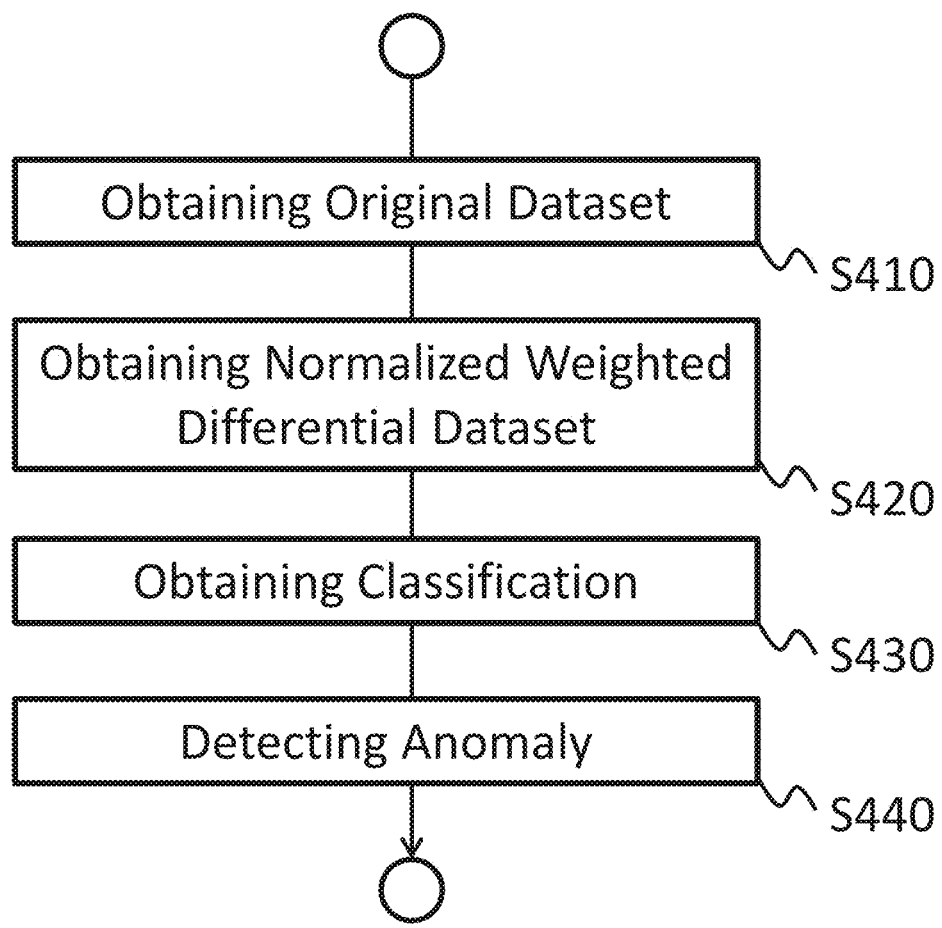
FIG. 9 shows a sub-flow of S300 in the flow of FIG. 5 according to the other embodiment of the present invention.

FIG. 9 shows a sub-flow of block S300 in the flow of FIG. 5 according to another embodiment of the present invention. The apparatus performs operations of blocks S410-S440 of FIG. 9 at the operation block S300 of FIG. 5.

At block S410, an obtaining section, such as the obtaining section 110, obtains the original dataset. In an embodiment, the original dataset may be image data such as 2D image data or 3D image data.

At block S420, a generating section, a calculating section, a determining section, a weighting section, and a normalizing section, such as the generating section 125, the calculating section 130, the determining section 135, the weighting section 140, and the normalizing section 145, obtain a normalized weighted differential dataset. In an embodiment, the apparatus may perform the operations of blocks S320-S390 explained in relation to FIG. 7, at block S420. At block S420, the determining section may determine ROI of the original dataset at an operation corresponding to block S340 in FIG. 7.

At block S430, a determining section obtains classification of the original dataset made by the classification model. The determining section may obtain the ROI of the original dataset made at block S420.

At block S440, the detecting section detects the anomaly by using the normalized weighted differential dataset obtained at block S420 and the classification of the original dataset obtained at block S430.

An exemplary algorithm for the embodiment of FIG. 8 will now be described. This exemplary algorithm is almost the same as the algorithm for the embodiment of FIG. 3A except that score is calculated from:

$$score = -\Sigma_i \Sigma_j loss_{(i,j)}^{sp} + f(x; \theta_r). \quad \text{Eq. (13)}$$

In an embodiment, the determining section may calculate $f(x; \theta_r)$ as a classification result at block S420. At block S440, the detecting section may calculate score and determine, in response, that score exceeds a threshold.

In the embodiments of FIGS. 8-9, the apparatus can detect anomalies by using outputs of both of the generative model and the classification model. Thereby, the apparatus may more accurately detect anomalies using less computational resources.

In the embodiments above, the normalizing section may normalize the integrated ROI. In other embodiments, the normalizing section may normalize the first output (shown as "1$^{st}$ ROI Output" in FIG. 3A and FIG. 8), and the second output (shown as "2$^{nd}$ ROI Output" in FIG. 3A and FIG. 8) before integrating them.

Figure 10:
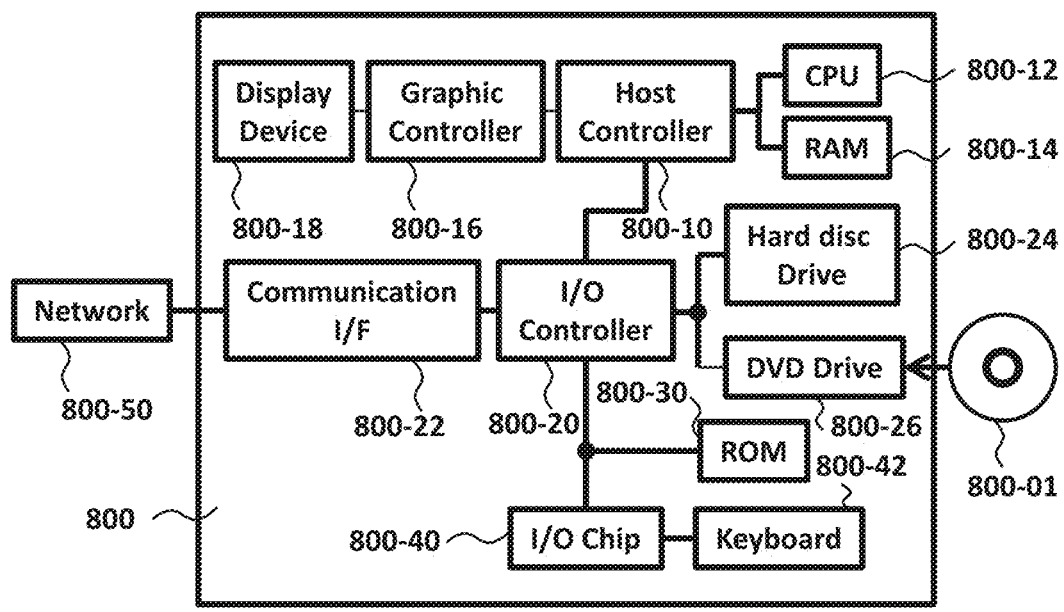
FIG. 10 shows an exemplary hardware configuration of a computer that functions as a system, according to an embodiment of the present invention.

FIG. 10 shows an exemplary hardware configuration of a computer configured for the embodiments of the present invention. A program that is installed in the computer 800 can cause the computer 800 to function as or perform operations associated with apparatuses of the embodiments of the present invention or one or more sections (including modules, components, elements, etc.) thereof, and/or cause the computer 800 to perform processes of the embodiments of the present invention or steps thereof. Such a program may be executed by the CPU 800-12 to cause the computer 800 to perform certain operations associated with some or all of the blocks of flowcharts and block diagrams described herein.

The computer 800 according to the present embodiment includes a CPU 800-12, a RAM 800-14, a graphics controller 800-16, and a display device 800-18, which are mutually connected by a host controller 800-10. The computer 800 also includes input/output units such as a communication interface 800-22, a hard disk drive 800-24, a DVD-ROM drive 800-26 and an IC card drive, which are connected to the host controller 800-10 via an input/output controller 800-20. The computer also includes legacy input/output units such as a ROM 800-30 and a keyboard 800-42, which are connected to the input/output controller 800-20 through an input/output chip 800-40.

The CPU 800-12 operates according to programs stored in the ROM 800-30 and the RAM 800-14, thereby controlling each unit. The graphics controller 800-16 obtains image data generated by the CPU 800-12 on a frame buffer or the like provided in the RAM 800-14 or in itself, and causes the image data to be displayed on the display device 800-18.

The communication interface 800-22 communicates with other electronic devices via a network 800-50. The hard disk drive 800-24 stores programs and data used by the CPU 800-12 within the computer 800. The DVD-ROM drive 800-26 reads the programs or the data from the DVD-ROM 800-01, and provides the hard disk drive 800-24 with the programs or the data via the RAM 800-14. The IC card drive reads programs and data from an IC card, and/or writes programs and data into the IC card.

The ROM 800-30 stores therein a boot program or the like executed by the computer 800 at the time of activation, and/or a program depending on the hardware of the computer 800. The input/output chip 800-40 may also connect various input/output units via a parallel port, a serial port, a keyboard port, a mouse port, and the like to the input/output controller 800-20.

A program is provided by computer readable media such as the DVD-ROM 800-01 or the IC card. The program is read from the computer readable media, installed into the hard disk drive 800-24, RAM 800-14, or ROM 800-30, which are also examples of computer readable media, and executed by the CPU 800-12. The information processing described in these programs is read into the computer 800, resulting in cooperation between a program and the above-mentioned various types of hardware resources. An apparatus or method may be constituted by realizing the operation or processing of information in accordance with the usage of the computer 800.

For example, when communication is performed between the computer 800 and an external device, the CPU 800-12 may execute a communication program loaded onto the RAM 800-14 to instruct communication processing to the communication interface 800-22, based on the processing described in the communication program. The communication interface 800-22, under control of the CPU 800-12, reads transmission data stored on a transmission buffering region provided in a recording medium such as the RAM 800-14, the hard disk drive 800-24, the DVD-ROM 800-01, or the IC card, and transmits the read transmission data to network 800-50 or writes reception data received from network 800-50 to a reception buffering region or the like provided on the recording medium.

In addition, the CPU 800-12 may cause all or a necessary portion of a file or a database to be read into the RAM 800-14, the file or the database having been stored in an external recording medium such as the hard disk drive 800-24, the DVD-ROM drive 800-26 (DVD-ROM 800-01), the IC card, etc., and perform various types of processing on the data on the RAM 800-14. The CPU 800-12 may then write back the processed data to the external recording medium.

Various types of information, such as various types of programs, data, tables, and databases, may be stored in the recording medium to undergo information processing. The CPU 800-12 may perform various types of processing on the data read from the RAM 800-14, which includes various types of operations, processing of information, condition judging, conditional branch, unconditional branch, search/replace of information, etc., as described throughout this disclosure and designated by an instruction sequence of programs, and writes the result back to the RAM 800-14.

In addition, the CPU 800-12 may search for information in a file, a database, etc., in the recording medium. For example, when a plurality of entries, each having an attribute value of a first attribute is associated with an attribute value of a second attribute, are stored in the recording medium, the CPU 800-12 may search for an entry matching the condition whose attribute value of the first attribute is designated, from among the plurality of entries, and reads the attribute value of the second attribute stored in the entry, thereby obtaining the attribute value of the second attribute associated with the first attribute satisfying the predetermined condition.

The above-explained program or software modules may be stored in the computer readable media on or near the computer 800. In addition, a recording medium such as a hard disk or a RAM provided in a server system connected to a dedicated communication network or the Internet can be used as the computer readable media, thereby providing the program to the computer 800 via the network.

The present invention may be a system, a method, and/or a computer program product. The computer program product may include a computer readable storage medium (or media) having computer readable program instructions thereon for causing a processor to carry out aspects of the present invention. The apparatus of the embodiments of the present invention may include the computer readable medium and the processor or programmable circuitry operable to execute the instructions.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to individualize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which includes one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and computer-implemented method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

As made clear from the above, the embodiments of the present invention enable anomaly detection based on region of interest.

What is claimed is:

1. A computer-implemented method, comprising:
   generating a reconstructed dataset from an original dataset by using a generative model;
   calculating a differential dataset between the original dataset and the reconstructed dataset as a differential dataset;
   determining a region of interest of the original dataset and a region of interest of the reconstructed dataset;
   weighting the differential dataset by using the determined region of interest;
   applying Gradient-weighted Class Activation Mapping (Grad-CAM) to obtain a Grad-CAM output as the region of interest of the original dataset and the region of interest of the reconstructed dataset; and
   detecting an anomaly by using the weighted differential dataset.

2. The method of claim 1, wherein the generative model is a Variational Auto Encoder.

3. The method of claim 1, wherein the determining of a region of interest of the original dataset and a region of interest of the reconstructed dataset, comprises:
   calculating an integration of the region of interest of the original dataset and the region of interest of the reconstructed dataset,
   wherein the weighting a differential dataset with the determined region of interest, comprises:
   weighting a differential dataset with the integration of the region of interest of the original dataset and the region of interest of the reconstructed dataset.

4. The method of claim 3, wherein the determining a region of interest of the original dataset and a region of interest of the reconstructed dataset, further comprises:
   classifying each of the original dataset and the reconstructed dataset as one of normal and anomalous by using a Convolutional Neural Network; and
   applying the Gradient-weighted Class Activation Mapping (Grad-CAM) to the Convolutional Neural Network to obtain the Grad-CAM output as the region of interest of the original dataset and the region of interest of the reconstructed dataset.

5. The method of claim 4, further comprising:
applying a first activating function, which returns a positive value in response to a negative value, to the region of interest of the original dataset to obtain a first output; and
applying a second activating function, which does not return a positive value to a negative value, to the region of interest of the reconstructed dataset to obtain a second output,
wherein the integration of the region of interest of the original dataset and the region of interest of the reconstructed dataset is a summation of the first output and the second output.

6. The method of claim 5, wherein the first activating function is an absolute value (ABS) function, and the second activating function is a Rectified Linear Unit (ReLU) function.

7. The method of claim 4, wherein the detecting the anomaly by using the weighted differential dataset, comprises: detecting the anomaly by using the weighted differential dataset and the classification of the original dataset.

8. The method of claim 1, further comprising: normalizing the weighted differential dataset before the detecting the anomaly by using the determined region of interest.

9. The method of claim 1, wherein the original dataset is an image data.

10. The method of claim 9, wherein the image data is 2D image data or 3D image data.

11. The method of claim 1, wherein the detecting the anomaly by using the weighted differential dataset, comprises:
calculating a summation of the weighted differential dataset; and
determining that the original dataset is anomalous in response to the summation exceeding a threshold.

12. The method of claim 1, wherein the detecting the anomaly by using the weighted differential dataset, comprises:
classifying the weighted differential dataset using a neural network; and
determining that the original dataset is anomalous on condition that the neural network classifies the weighted differential dataset as anomalous.

13. An apparatus comprising:
a processor or a programmable circuitry; and
one or more computer readable mediums collectively including instructions that, when executed by the processor or the programmable circuitry, cause the processor or the programmable circuitry to perform operations including:
generating a reconstructed dataset from an original dataset by using a generative model;
calculating a differential dataset between the original dataset and the reconstructed dataset as a differential dataset;
determining a region of interest of the original dataset and a region of interest of the reconstructed dataset;
weighting the differential dataset by using the determined region of interest;
applying Gradient-weighted Class Activation Mapping (Grad-CAM) to obtain a Grad-CAM output as the region of interest of the original dataset and the region of interest of the reconstructed dataset; and
detecting an anomaly by using the weighted differential dataset.

14. The apparatus of claim 13, wherein the generative model is a Variational Auto Encoder.

15. The apparatus of claim 13, wherein the determining a region of interest of the original dataset and a region of interest of the reconstructed dataset, comprises:
calculating an integration of the region of interest of the original dataset and the region of interest of the reconstructed dataset,
wherein the weighting a differential dataset with the determined region of interest, comprises:
weighting a differential dataset with the integration of the region of interest of the original dataset and the region of interest of the reconstructed dataset.

16. The apparatus of claim 15, wherein the determining a region of interest of the original dataset and a region of interest of the reconstructed dataset, further comprises:
classifying each of the original dataset and the reconstructed dataset as one of normal and anomaly by using a Convolutional Neural Network; and
applying the Gradient-weighted Class Activation Mapping (Grad-CAM) to the Convolutional Neural Network to obtain the Grad-CAM output as the region of interest of the original dataset and the region of interest of the reconstructed dataset.

17. A computer program product including one or more computer readable storage mediums collectively storing program instructions that are executable by a processor or programmable circuitry to cause the processor or programmable circuitry to perform operations comprising:
generating a reconstructed dataset from an original dataset by using a generative model;
calculating a differential dataset between the original dataset and the reconstructed dataset as a differential dataset;
determining a region of interest of the original dataset and a region of interest of the reconstructed dataset;
weighting the differential dataset by using the determined region of interest;
applying Gradient-weighted Class Activation Mapping (Grad-CAM) to obtain a Grad-CAM output as the region of interest of the original dataset and the region of interest of the reconstructed dataset; and
detecting an anomaly by using the weighted differential dataset.

18. The computer program product of claim 17, wherein the generative model is a Variational Auto Encoder.

19. The computer program product of claim 17, wherein the determining a region of interest of the original dataset and a region of interest of the reconstructed dataset, comprises:
calculating an integration of the region of interest of the original dataset and the region of interest of the reconstructed dataset,
wherein the weighting a differential dataset with the determined region of interest, comprises:
weighting a differential dataset with the integration of the region of interest of the original dataset and the region of interest of the reconstructed dataset.

20. The computer program product of claim 19, wherein the determining a region of interest of the original dataset and a region of interest of the reconstructed dataset, further comprises:
classifying each of the original dataset and the reconstructed dataset as one of normal and anomaly by using a Convolutional Neural Network; and applying the Gradient-weighted Class Activation Mapping (Grad-CAM) to the Convolutional Neural Network to obtain the Grad-CAM output as the region of interest of the original dataset and the region of interest of the reconstructed dataset.

* * * * *